United States Patent
Duffy et al.

(10) Patent No.: US 12,290,398 B2
(45) Date of Patent: May 6, 2025

(54) AUTOMATED DETECTION OF LUNG SLIDE TO AID IN DIAGNOSIS OF PNEUMOTHORAX

(71) Applicants: FUJIFILM SONOSITE, INC., Bothell, WA (US); MASS GENERAL BRIGHAM, Boston, MA (US)

(72) Inventors: Thomas Michael Duffy, Bothell, WA (US); Davinder S. Dhatt, Bothell, WA (US); Paul Tomotaro Danset, Bothell, WA (US); Adam Benjamin Pely, Bothell, WA (US); Christopher Alexksandr White, Bothell, WA (US); Diku Pranav Mandavia, Bothell, WA (US); Quanzheng Li, Belmont, MA (US); Andrew Liteplo, Chestnut Hill, MA (US); Kyungsang Kim, Boston, MA (US); Suzannah McKinney, Boston, MA (US); Fabiola Macruz, Boston, MA (US)

(73) Assignees: FUJIFILM SONOSITE, INC., Bothell, WA (US); MASS GENERAL BRIGHAM, Boston, MA (US)

(*) Notice: Subject to any disclaimer, the term of this patent is extended or adjusted under 35 U.S.C. 154(b) by 377 days.

(21) Appl. No.: 17/734,586

(22) Filed: May 2, 2022

(65) Prior Publication Data
US 2023/0346337 A1 Nov. 2, 2023

(51) Int. Cl.
*A61B 8/08* (2006.01)
*A61B 8/00* (2006.01)
(Continued)

(52) U.S. Cl.
CPC ............. *A61B 8/085* (2013.01); *A61B 8/463* (2013.01); *A61B 8/486* (2013.01); *A61B 8/5207* (2013.01);
(Continued)

(58) Field of Classification Search
CPC ......... A61B 8/085; A61B 8/463; A61B 8/486; A61B 8/5207; G06T 7/55; G06T 5/70;
(Continued)

(56) References Cited

U.S. PATENT DOCUMENTS

| | | | |
|---|---|---|---|
| 2017/0091914 A1* | 3/2017 | Halmann | A61B 8/4245 |
| 2019/0105013 A1* | 4/2019 | Wang | A61B 8/463 |

(Continued)

FOREIGN PATENT DOCUMENTS

| | | |
|---|---|---|
| WO | 2020037266 A1 | 2/2020 |
| WO | 2022016262 A1 | 1/2022 |

OTHER PUBLICATIONS

Jascur et al.: "Detecting the Absence of Lung Sliding in Lung Ultrasounds Using Deep Learning", Jul. 29, 2021, 14 pages.
(Continued)

*Primary Examiner* — Michael R Neff
(74) *Attorney, Agent, or Firm* — Womble Bond Dickinson (US) LLP

(57) ABSTRACT

Methods and apparatuses for performing automated detection of lung slide using a computing device (e.g., an ultrasound system, etc.) are disclosed. In some embodiments, the techniques determine lung sliding using one or more neural networks. In some embodiments, the neural networks are part of a process that determines probabilities of the lung sliding at one or more M-lines. In some embodiments, the techniques display one or more probabilities of lung sliding in a B-mode ultrasound image.

17 Claims, 12 Drawing Sheets

(51) Int. Cl.
  *G06T 5/50* (2006.01)
  *G06T 5/70* (2024.01)
  *G06T 7/00* (2017.01)
  *G06T 7/20* (2017.01)
  *G06T 7/55* (2017.01)

(52) U.S. Cl.
  CPC .................. *G06T 5/50* (2013.01); *G06T 5/70* (2024.01); *G06T 7/0014* (2013.01); *G06T 7/20* (2013.01); *G06T 7/55* (2017.01); *G06T 2207/10132* (2013.01); *G06T 2207/20084* (2013.01); *G06T 2207/20212* (2013.01); *G06T 2207/30061* (2013.01); *G06T 2207/30168* (2013.01)

(58) Field of Classification Search
  CPC ........... G06T 5/50; G06T 7/0014; G06T 7/20; G06T 2207/10132; G06T 2207/20084; G06T 2207/20212; G06T 2207/30061; G06T 2207/30168
  USPC ....................................................... 382/128
  See application file for complete search history.

(56) References Cited

U.S. PATENT DOCUMENTS

| | | |
|---|---|---|
| 2019/0150889 A1 | 5/2019 | Xu et al. |
| 2020/0054306 A1* | 2/2020 | Mehanian ............ A61B 8/5223 |
| 2020/0074625 A1* | 3/2020 | Østvik ................. G06F 18/211 |

OTHER PUBLICATIONS

PCT International Search Report and The Written Opinion Of The International Searching Authority for PCT/US2023/017553, mailed Jul. 31, 2023, 10 pages.

* cited by examiner

AUTOMATED DETECTION OF LUNG SLIDE TO AID IN DIAGNOSIS OF PNEUMOTHORAX

FIELD OF THE INVENTION

The embodiments disclosed herein relate generally to ultrasound imaging; more specifically, the embodiments disclosed herein relate to performing automated detection of lung slide using ultrasound imaging systems including the generation of visualizations (e.g., three-dimensional images) that indicate the presence of lung sliding.

BACKGROUND

Lung ultrasound (US) represents a novel and promising approach for aiding in the diagnosis of Pneumothorax (PTX), with high sensitivity and specificity. More specifically, a determination of lung sliding or non-sliding can aid in the diagnosis of PTX, and the diagnosis of PTX using ultrasound equipment has been done and is determined using lung sliding/non-sliding metrics. The metrics usually involve motion with respect to a pleural line in an ultrasound image. Currently, clinicians evaluate the B-mode video clips for motion above and below the pleural line. Additionally, clinicians use M-mode to look at the motion above and below the pleural line. These techniques have disadvantages in that they must be done by someone skilled in recognizing lung sliding and/or are time consuming and prone to user error. These disadvantages could prevent the use of these techniques in real-time in certain situations, which could impact lifesaving efforts.

SUMMARY

Methods and apparatuses for performing automated detection of lung slide using a computing device (e.g., an ultrasound system, etc.) are disclosed. In some embodiments, the methods are implemented by a computing device.

In some embodiments, the method for determining lung sliding includes generating attribute quality probabilities for B-mode ultrasound images that include a pleural line and determining, based on the attribute quality probabilities, a quality level of the B-mode ultrasound images as acceptable for said determining the lung sliding. The method also includes generating one or more M-mode ultrasound images based on the B-mode ultrasound images and generating one or more probabilities of the lung sliding based on the one or more M-mode ultrasound images.

In some embodiments, the method for determining lung sliding includes generating B-mode ultrasound images and generating an M-mode ultrasound image corresponding to an M-line. The method also includes generating, based on the M-mode ultrasound image, a probability of the lung sliding at the M-line and indicating in at least one B-mode ultrasound image of the B-mode ultrasound images the probability of the lung sliding.

In some embodiments, a computing device implements an ultrasound system for determining lung sliding. In some embodiments, the computing device includes: a memory to maintain B-mode ultrasound images and one or more M-mode ultrasound images; and a neural network implemented at least partially in hardware of the computing device to generate, based on the one or more M-mode ultrasound images, one or more probabilities of the lung sliding at one or more M-lines. The computing device also includes a processor system to: generate, based on pixels in the B-mode ultrasound images that correspond to the one or more M-lines, the one or more M-mode ultrasound images corresponding to the one or more M-lines; and cause display in at least one of the B-mode ultrasound images of one or more representations of the one or more probabilities of the lung sliding.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Techniques are disclosed herein to automatically detect lung sliding in ultrasound images generated with ultrasound systems. The detection of lung sliding may be used for aiding in the diagnosis of Pneumothorax (PTX). The automated detection of lung sliding on US can improve diagnostic accuracy and speed, as well as decrease patient management time.

In some embodiments, the ultrasound system automatically detects lung sliding or non-lung sliding in ultrasound images through the use of one or more neural networks. These neural networks use trained models to determine lung sliding to help reduce operator to operator variability and implement a consistent algorithm for detection of lung sliding. In some embodiments, the neural networks aid the user by acquiring video clips with acceptable quality to determine the presence of sliding in the lung.

By automatically detecting lung sliding, the ability to diagnose PTX in real-time with portable ultrasound equipment can have lifesaving impacts, as the use of ultrasound equipment would enable the diagnosis of PTX at the point of care without needing to send patients or images to the radiology department. Furthermore, automated detection of lung sliding can improve diagnostic accuracy and speed, as well as decrease patient management time.

Example automated detection algorithms and implementations are discussed in greater detail below.

Figure 1:
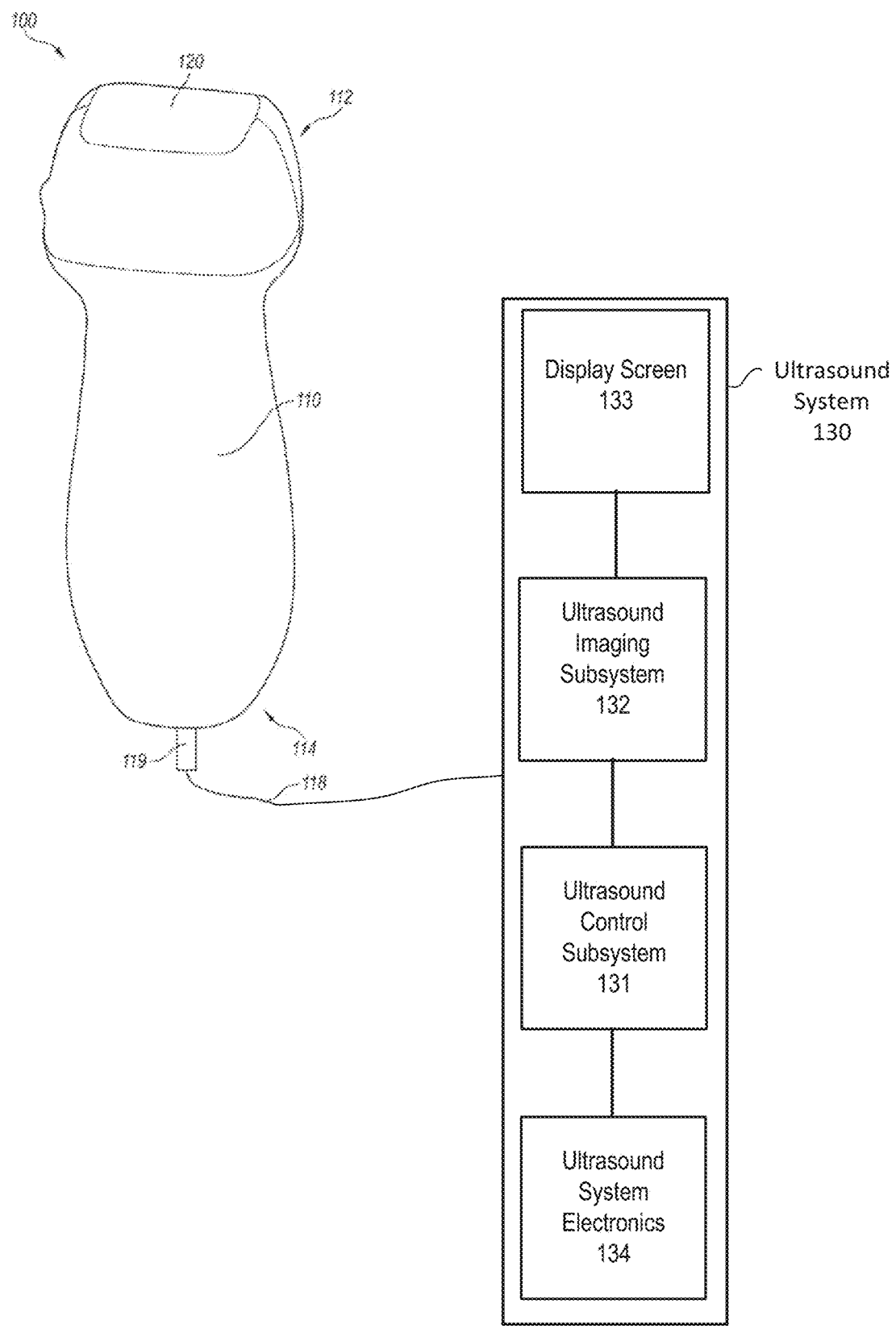
FIG. 1 illustrates some embodiments of an ultrasound machine.

FIG. 1 illustrates some embodiments of an ultrasound machine with an embodiment of the disclosed technology. Referring to FIG. 1, ultrasound transducer probe 100 includes an enclosure 110 extending between a distal end portion 112 and a proximal end portion 114. The ultrasound transducer probe 100 is electrically coupled to an ultrasound imaging system 130 via a cable 118 that is attached to the proximal end of the probe by a strain relief element 119. In some embodiments, ultrasound transducer probe 100 is electrically coupled to an ultrasound imaging system 130 wirelessly.

A transducer assembly 120 having one or more transducer elements is electrically coupled to the system electronics in ultrasound imaging system 130. In operation, transducer assembly 120 transmits ultrasound energy from the one or more transducer elements toward a subject and receives ultrasound echoes from the subject. The ultrasound echoes are converted into electrical signals by the one or more transducer elements and electrically transmitted to the system electronics in ultrasound imaging system 130 to form one or more ultrasound images.

Capturing ultrasound data from a subject using an exemplary transducer assembly (e.g., the transducer assembly 120) generally includes generating ultrasound, transmitting ultrasound into the subject, and receiving ultrasound reflected by the subject. A wide range of frequencies of ultrasound may be used to capture ultrasound data, such as, for example, low frequency ultrasound (e.g., less than 15 MHz) and/or high frequency ultrasound (e.g., greater than or equal to 15 MHz) can be used. Those of ordinary skill in the art can readily determine which frequency range to use based on factors such as, for example, but not limited to, depth of imaging and/or desired resolution.

In some embodiments, ultrasound imaging system 130 includes ultrasound system electronics 134 that comprises one or more processors, integrated circuits, ASICs, FPGAs, and power sources to support the functioning of ultrasound imaging system 130 in a manner well-known in the art. In some embodiments, ultrasound imaging system 130 also includes ultrasound control subsystem 131 having one or more processors. At least one processor, FPGA, or ASIC causes electrical signals to be sent to the transducer(s) of probe 100 to emit sound waves and also receives the electrical pulses from the probe that were created from the returning echoes. One or more processors, FPGAs, or ASICs processes the raw data associated with the received electrical pulses and forms an image that is sent to ultrasound imaging subsystem 132, which displays the image on display screen 133. Thus, display screen 133 displays ultrasound images from the ultrasound data processed by the processor of ultrasound control subsystem 131.

In some embodiments, the ultrasound system can also have one or more user input devices (e.g., a keyboard, a cursor control device, microphone, camera, etc.) that inputs data and allows the taking of measurements from the display of the ultrasound display subsystem, a disk storage device (e.g., hard, floppy, thumb drive, compact disks (CD), digital video discs (DVDs)) for storing the acquired images, and a printer that prints the image from the displayed data. These devices also have not been shown in FIG. 1 to avoid obscuring the techniques disclosed herein.

In some embodiments, ultrasound system electronics 134 performs automated detection of lung sliding. The automated detection of whether lung sliding is present or not may aid clinicians in diagnosing or ruling out Pneumothorax and includes benefits such as improved diagnostic accuracy and speed, decreased patient management time, reduced operator-to-operator variability resulting from use of a consistent algorithm for lung sliding.

In some embodiments, the automated detection of lung sliding is performed using an automated artificial intelligence (AI) algorithm that relies on the observation of multiple frames to determine if sliding is present and its location within the body. In some embodiments, the automated detection is performed by sending a series of images to a neural network (e.g., a convolutional neural network (CNN), Swin Transformer, etc.). The series of images may be ultrasound video clips and may be sent as either a collection of stacked images into a single CNN, a series of images into a RNN (Recurrent neural network), or a time-based AI model that is able to provide an indication (e.g., a probability) of whether the images show that lung sliding is present. Given appropriate training data involving fully annotated images of where sliding exists in each image, the model could learn to detect sliding and its location in the images. In some embodiments, as opposed to examining the frames as a whole, the automated detection process examines single lines of the data. The single lines of data may be M-lines from M-mode images. These M-mode images may be generated in a number of ways. For example, the M-mode images may be obtained through M-mode acquisition where a collection of a single line of data is acquired at a fixed rate (for example 100 lines per second) for a period of time (for example one second equals 100 data lines). Additionally or alternatively the M-mode images may be obtained by creating them from B-mode images.

In some embodiments, the automated detection process detects lung sliding from this single M-mode strip (hereinafter "M-strip") by creating one or more M-mode images based on one or more M-lines. That is, an M-strip is a sequence of 3 B-mode frames out of which M-mode images are extracted at various M-lines. Details of these embodiments are described in more detail below. In some embodiments, the automated detection uses a neural network to examine the single M-strip to determine if there is motion above and below the pleural line, thereby indicating that the lung has not collapsed. In some embodiments, if the acquisition frame rate is high enough, the automated detection process extracts multiple M-strips from a collection of B-mode images (e.g., two-dimensional (2-D) video clips, etc.) and uses a neural network to detect lung sliding from the M-strips. In some embodiments, the automated detection process extracts M-mode lines at an angle to the vertical from each B-mode image in a technique often referred to as anatomical M-mode and uses a neural network to examine these lines to determine if lung sliding is present. In both these cases, the neural network has a model that is trained using appropriate training data involving fully annotated images of where sliding exists in each image and learns to detect sliding and its location in input images.

Figure 2B:
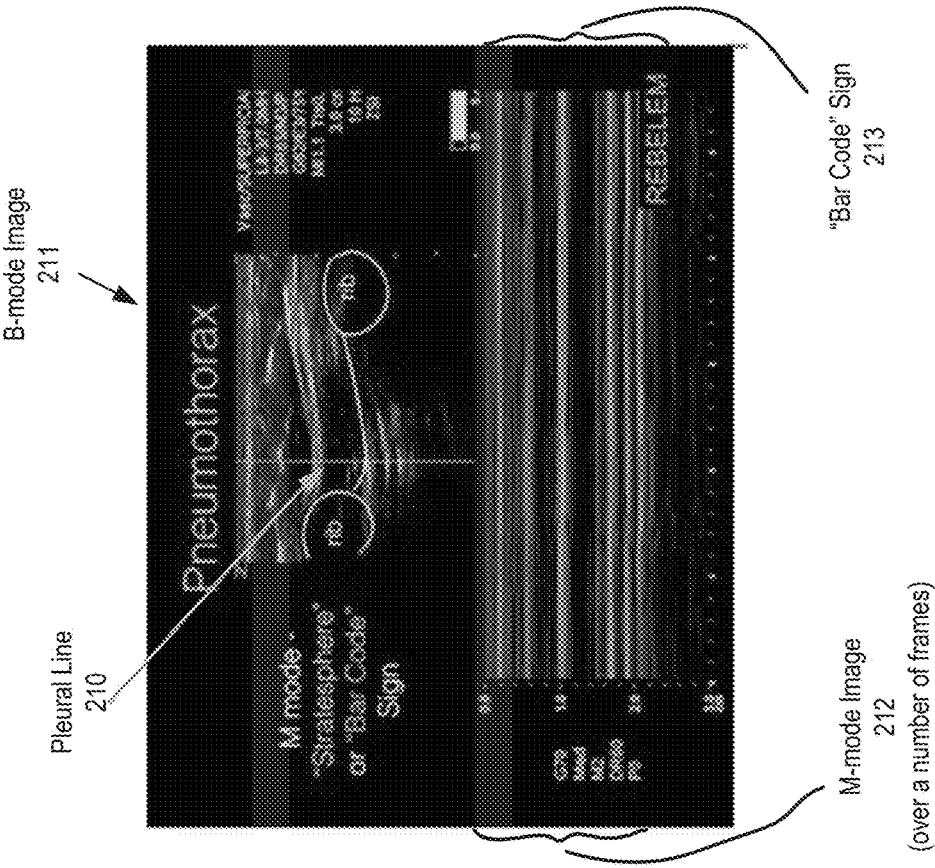
FIGS. 2A and 2B illustrate examples of B-mode images.
Figure 2A:
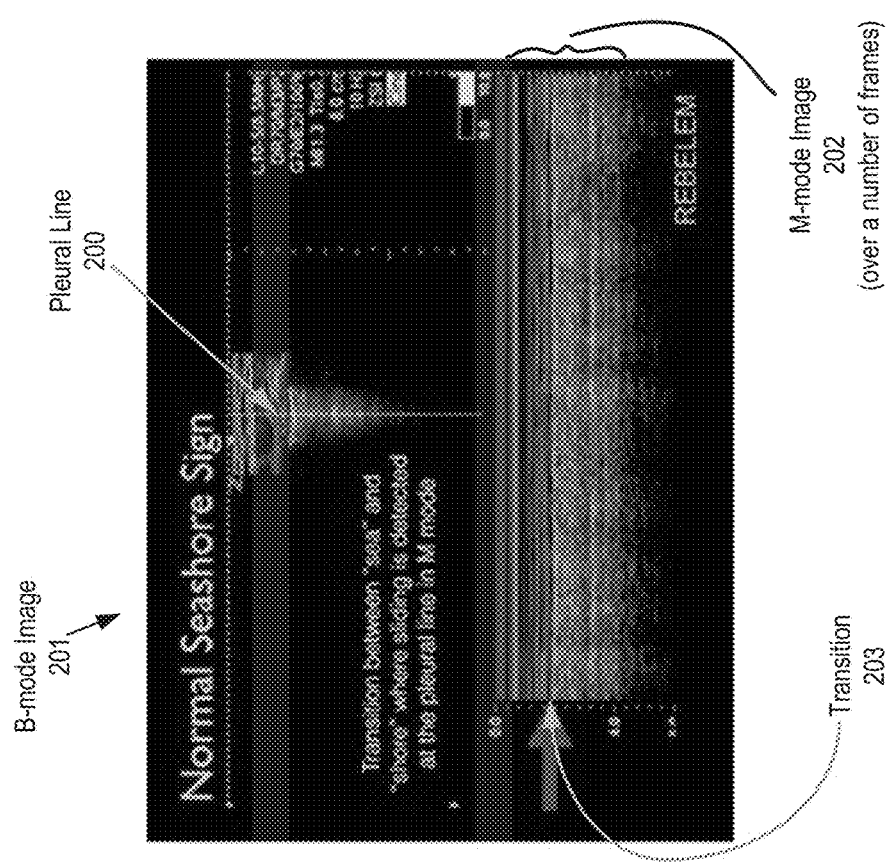

FIGS. 2A and 2B illustrate examples of a B-mode image with a selected horizontal position (illustrated in the top middle portion of the figure) and an M-strip at that location over a number of frames (illustrated below the B-mode image in the figure). In some embodiments, the M-strip is a 3-dimensional array of data (e.g., x and y dimensions of the B-mode image along with the z dimension of time—i.e. frames). In some embodiments, the M-strip is extracted from a sequence of B-mode images and the M-mode image is reconstructed from 2-D ultrasound video clips.

A lung with-lung sliding (i.e., a lung which indicates a normal aeration pattern in an inflating and deflating lung) can be shown in an M-mode pattern of uninterrupted horizontal lines superficial to the pleural surface with a granular pattern deep to this level. This is sometimes referred to as a "seashore sign". FIG. 2A illustrates a "seashore sign" in which there is a transition 203 between the "sea" and the "shore" where sliding is detected at pleural line 200 in M-mode image 202 (generated from a number of frames of B-mode images 201) as indicated by the motion above and below pleural line 200 of B-mode image 201. In contrast, FIG. 2B illustrates pneumothorax (PTX) with a pattern sometimes called the "stratosphere" or "bar code" sign 213 in an M-mode image 212 (generated from a number of frames from B-mode images 211), indicating that there is no motion and thus no lung sliding at pleural line 210 in B-mode image 210.

Using a neural network to automatically detect lung sliding by examining ultrasound images has a number of benefits, including, but not limited to, its computational requirements are small and the data is easy to annotate (i.e., is sliding, or is not sliding).

One challenge with an automated detection process that uses M-mode lines is determining what lines to test. In some embodiments, the determination of which lines to test is done by first identifying a region of interest (ROI) in an image where M-mode images should be extracted (e.g., suitable to extract M-lines) and tested. That is, the ROI indicates the set of M-lines from which a selection made be made to extract M-mode images. For example, any of the M-line locations (i.e. X image location) between the left and right portions of the ROI, and once the M-lines are selected, M-mode images are extracted from that M-strip at those M-lines (i.e. X) locations. In some embodiments, as discussed above, this ROI spans the pleural line in a rib space of the lung. In one example, more than one M-line from the region is tested to improve the accuracy of the sliding determination. It is also likely that different regions of the lung will have different levels of sliding depending on the severity of the PTX observed.

Example Automatic Detection Embodiments

In some embodiments, the automated detection process has a number of processes including determining image quality for lung sliding detection, determining an ROI for lung sliding detection, determining an acceptable image quality for M-mode reconstruction regions, and determining lung sliding detection. Each of these operations is described in more detail below.

Determination of Image Quality and Region of Interest (ROI) for Lung Sliding Detection To ensure that the lung sliding detection is evaluated on acceptable images, an AI model referred to herein as a neural network (e.g., a CNN, etc.) is trained to recognize images that have acceptable quality and an appropriate view for use in automated detection of lung sliding. In some embodiments, the determination of acceptable quality is based on one or more factors, such as but not limited to resolution, gain, brightness, clarity, centeredness, depth, recognition of the pleural line, and recognition of a rib and/or rib shadow.

In some embodiments, the neural network recognizes appropriate views by recognizing the images that have such expected features as a pleural line and ribs in the image. For example, in some embodiments, the neural network recognizes a clear pleural line in the upper middle region of an image and seeing at least one rib shadow on one of the sides of the image. In one embodiment, the neural network is trained to recognize the locations of the pleural line via different methods. These methods include, but are not limited to, the use of two points at the extents of the pleural line, left and right extents and center depth, a segmentation map, and a heat map.

Figure 3B:
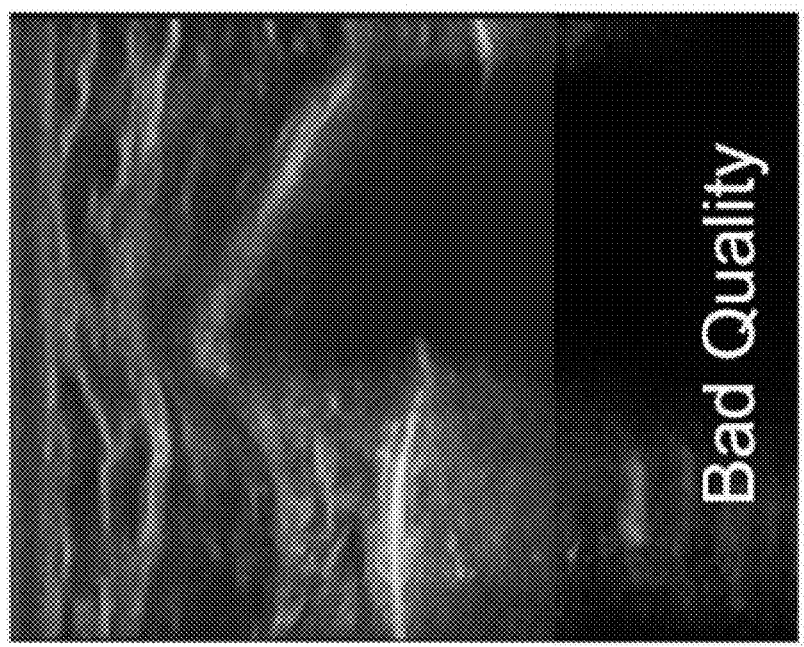
FIG. 3B illustrates an example of a bad quality image.
Figure 3A:
FIG. 3A illustrates an example of a good quality image.

In some embodiments, data output from the neural network, combined with heuristics, can be used to determine images that are acceptable, or good quality, or determine that images are not acceptable, or bad quality. FIG. 3A illustrates an example of a good quality image. The neural network may determine an image is not acceptable, as having bad quality, because of one or more of its attributes such as, for example, images that are too dark, too bright, too fuzzy, too deep, too shallow, not centered, in addition to not recognizing expected features such as the pleural line and ribs; and the neural network may determine that an image is acceptable, e.g., as having good quality, when it does not have any of these attributes that made the image unacceptable. FIG. 3A illustrates an example of a good quality image. FIG. 3B illustrates an example of a poor-quality image. In some embodiments, the neural network outputs the good and bad quality indications as good/bad probability for a number of attributes.

Figure 4:
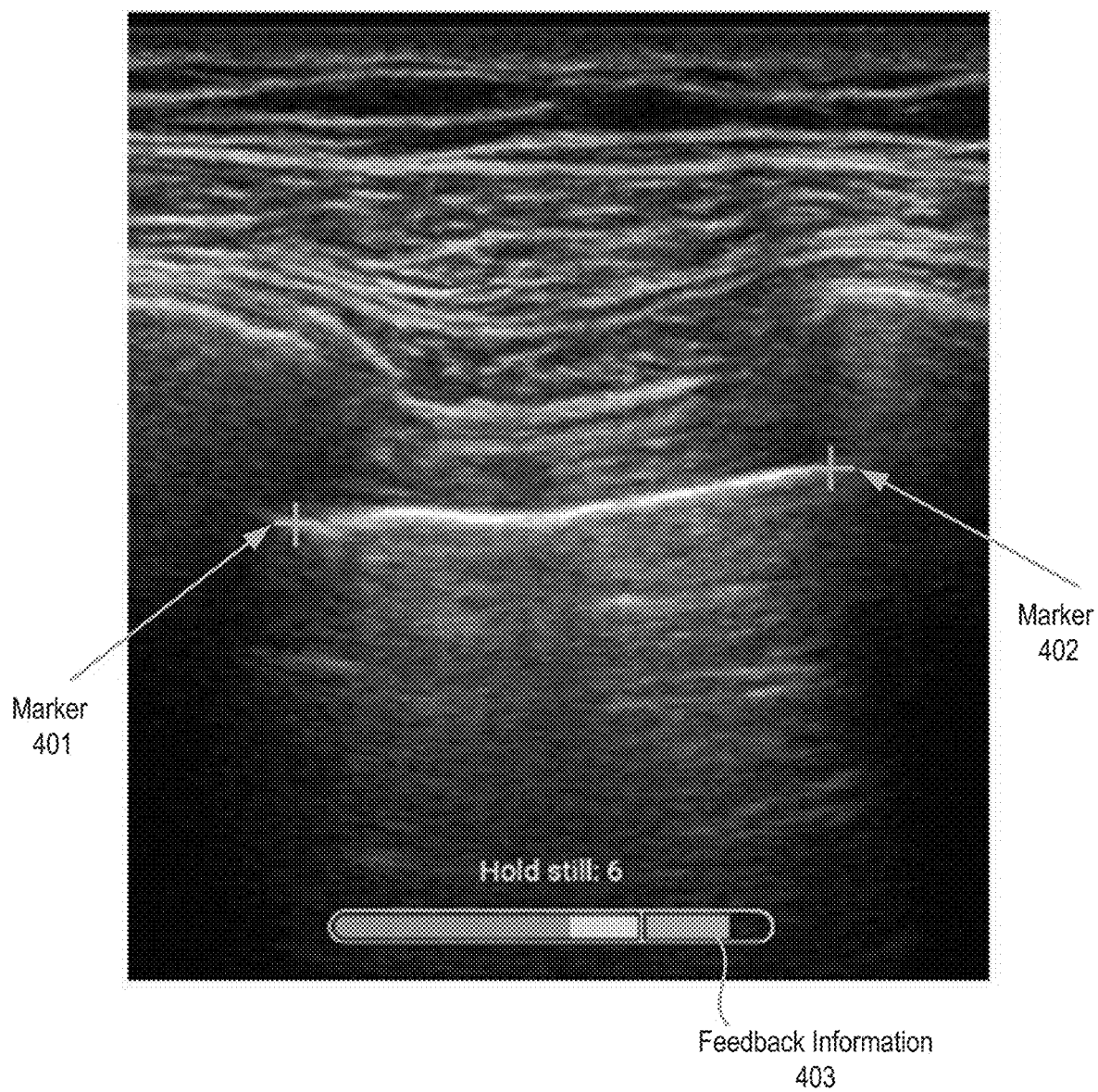
FIG. 4 illustrates an example of a pleural line.

In addition to computing a good/bad probability for a number of attributes, the neural network can also detect the location of the two points (e.g., x,y locations or coordinates) that mark the left and right edges, or end points, of the pleural line in the image. FIG. 4 illustrates an example of a pleural line. Referring to FIG. 4, markers 401 and 402 indicate the end points of the pleural line.

In some embodiments, to determine the overall quality of a B-mode ultrasound image, the good/bad probability generated by the neural network is used in combination with heuristic rules that use the x/y locations of the pleural line. In some embodiments, the x locations are used to determine if the pleural line spans a prescribed distance within the image. In some embodiments, the prescribed distance is based on the percentage of the image centered on the center of the image. For example, the line segment made by connecting the ROI points must cross the center of the image. If the pleural line does not span the prescribed distance, then the image is considered bad. The y locations of the pleural line can be used to determine if the image is too deep or too shallow. The location information can be used to determine the region of interest (ROI) over which a metric for lung sliding is computed. For instance, the x locations of the pleural line from the model can be used to determine a ROI that can be used to select M-line locations for reconstructed M-mode images.

Determination of Acceptable Quality for M-Mode Reconstruction Regions (M-Strips)

M-mode images can be reconstructed from an M-strip. Before constructing M-mode images from the M-strip, the frames are examined to determine if the M-strip is acceptable for determining lung sliding. This determination can be based on the reported quality of each frame in the M-strip being of good quality. Additionally or alternatively, in some embodiments, the lung sliding detection process examines ROI points to determine if there is too much motion. Excessive motion can make it difficult to determine if there is lung sliding or not in the reconstructed M-mode. By looking for excessive motion, the M-strip is marked as having good or bad quality. If the M-strip quality is bad, then it would not be used for lung sliding detection. In some embodiments, to detect motion within the M-strip frames, the change in the x,y locations of the pleural line in consecutive B-mode frames can be compared to each other to see if it exceeds a prescribed limit. If the change in the x,y locations of the pleural line exceeds the prescribed limit, then the motion of the M-strip frame is too much for use in determining if lung sliding exists or not. Note that this determination of whether this is too much gross motion in the B-mode images to use it for lung sliding detection may be made by a neural network. For example, the neural network can look at ROIs on every frame and if there is misalignment of the points throughout the frames, then the neural network would determine that the M-mode images reconstructed from the B-mode images would not be of good enough quality.

Once an M-strip is designated as good quality, then M-mode images can be reconstructed for any of the M-lines in the B-mode Image within the ROI. In some embodiments, the M-mode images may be reconstructed by taking the vertical image pixels for a given M-line column from each frame (e.g., 25 frames) in the M-strip. This process can be repeated for all selected frames. Combining these vertical columns produces a M-mode image with a pulse repetition frequency (PRF) equal to the frame rate of the video clip.

Figure 5A:
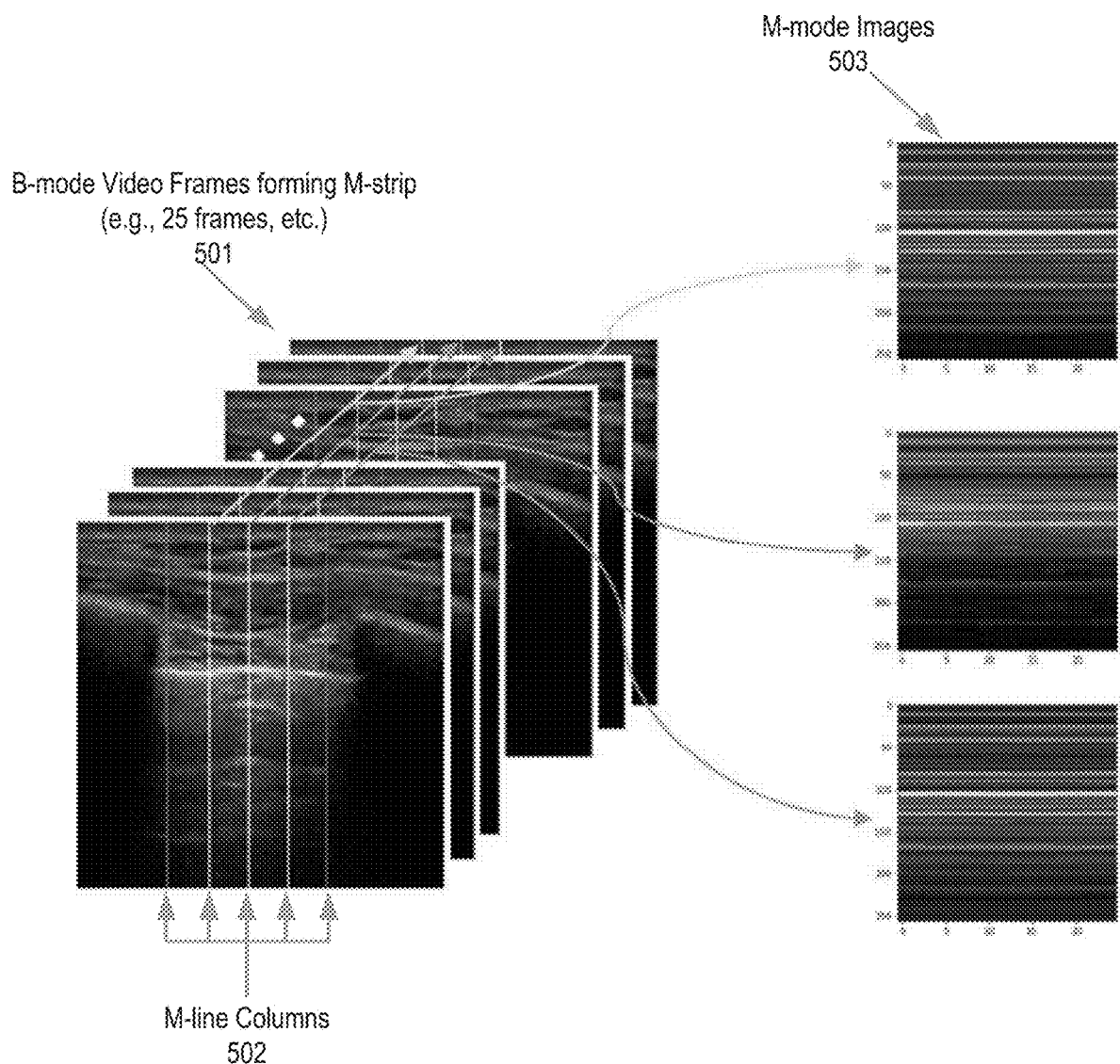
FIG. 5A illustrates M-mode images being constructed from M-line columns of B-mode video frames.

FIG. 5A illustrates M-mode images being constructed from M-line columns of B-mode video frames. Referring to FIG. 5A, B-mode video frames forming M-strip 501 (e.g., 25 frames, etc.) are shown with M-line columns 502 highlighted. The same column of M-line columns 502 in each of the B-mode video frames 501 is combined to create the M-mode images 503. While FIG. 5A only shows three M-mode images 503, there may be less than or greater than three M-mode images 503 created from M-line columns 502 of B-mode video frames 501. Note that lung sliding can be performed by evaluating multiple M-mode images constructed in this manner. For example, a window that is three or more pixels wide may be examined as a region of interest in the M-mode images 509. This window may be a sliding window that is examined to make a determination on whether lung sliding does or does not exist somewhere in that region.

Alternatively or additionally to constructing M-mode images as described above, the lung sliding detection process can be run and lung sliding can be detected on stored images (e.g., a CINE loop having a sequence of digital images from an ultrasound examination, etc.).

Determination of Lung Sliding

In some embodiments, a second neural network is trained to discriminate between M-mode images that indicate lung sliding and M-mode images that indicate that there is no lung sliding. The reconstructed M-mode images are fed into this model to determine if there is sliding or not. In some embodiments, this determination is made based on only one M-mode image. In some embodiments, this determination is made based on multiple M-mode images. For example, depending on the available computing resources and response time, the ultrasound system can construct a variable number of M-mode images and pass them through the lung sliding model to determine if there is sliding or not. This detection can be done for a number of M-mode images that are constructed from different M-line locations within the M-strip. This detection can also be done for a number of M-strips (e.g., different sequences of B-mode images that may or may not be contiguous in time). All of the lung sliding detection outputs can be combined in such a way as to get a higher average accuracy than when looking at the lung sliding model detection from a single reconstructed M-mode. In some embodiments, the lung sliding detection outputs are combined using a mean function to achieve high accuracy.

Figure 5B:
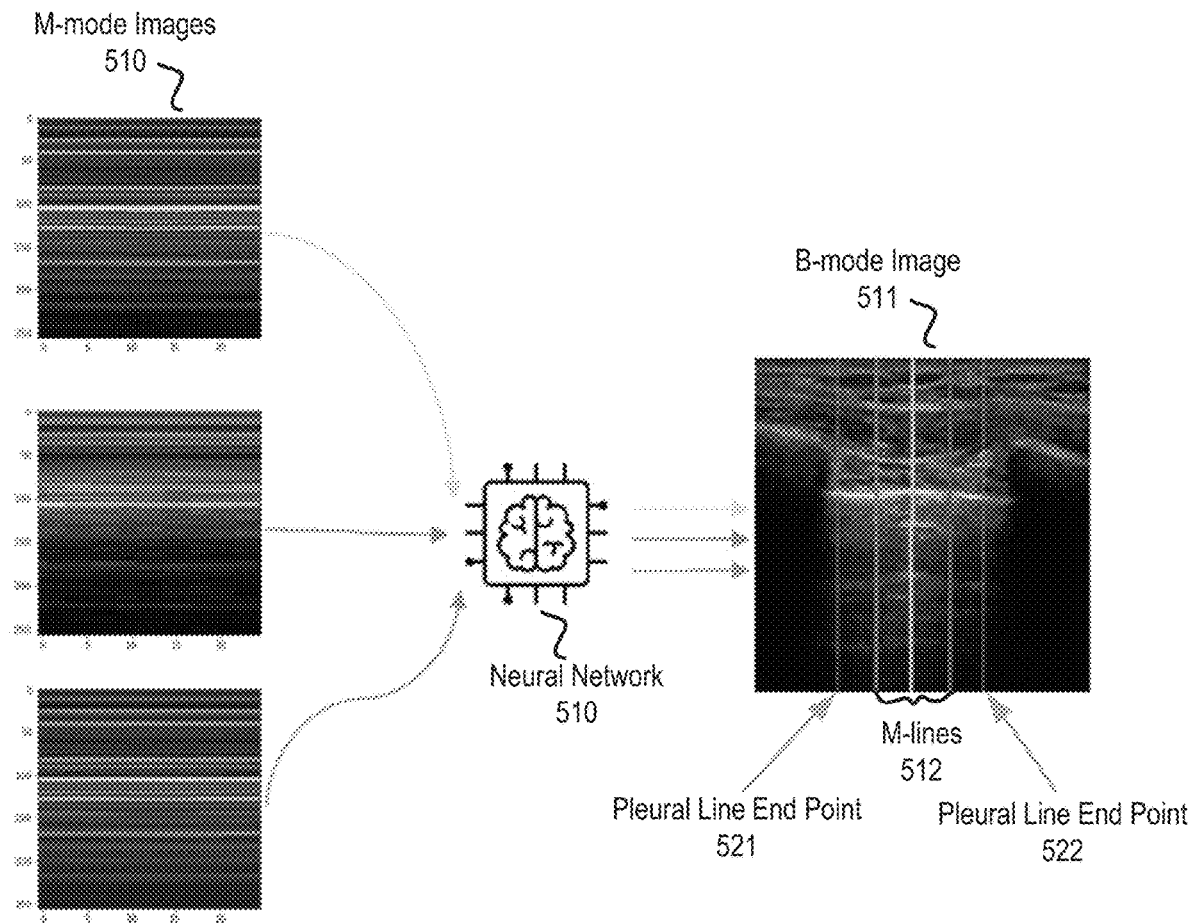
FIG. 5B shows the processing of the M-mode images with a neural network to generate probabilities of lung sliding at three M-lines.

FIG. 5B shows the processing of the M-mode images with a neural network to generate probabilities of lung sliding at three M-lines. Referring to FIG. 5B, M-mode images 510 are input to neural network 510 to produce B-mode image 511 with M-lines 512 between pleural line end points 521 and 522. The M-mode images 510 are examples of M-mode images generated from an M-strip of B-mode images, such as M-mode images 503 in FIG. 5A, while M-lines 512 are examples of M-lines taken from a M-stripe such as M-line columns 502 of M-strip 501. While FIG. 5B surely shows three mode images 510 being input to neural network 510, in alternative embodiments, more or less than three M-mode images may be input into neural network to detect lung sliding.

In some embodiments, M-lines 512 are displayed in the B-mode image 511 with an indication indicating the probability of lung sliding or not. For example, one of M-lines 512 can be a particular gradient color (e.g., green) to indicate sliding, while another one of the M-lines 511 can be displayed on the B-mode image 511 with a gradient color indicating low or no probability of lung sliding (e.g., red). In this case illustrated in FIG. 5B, M-lines 512 that are displayed equal three in number. However, the techniques described here are not limited to displaying only three M-lines. Note that there may be an M-line 512 for every line in the M-mode images 510. In such a case, the lines could indicate the start of lung sliding to a portion where there is no lung sliding. Additionally or alternatively, a user may select which M-lines are to be indicated in the B-mode image 511.

An Example of a Lung Sliding Detection System

Figure 6:
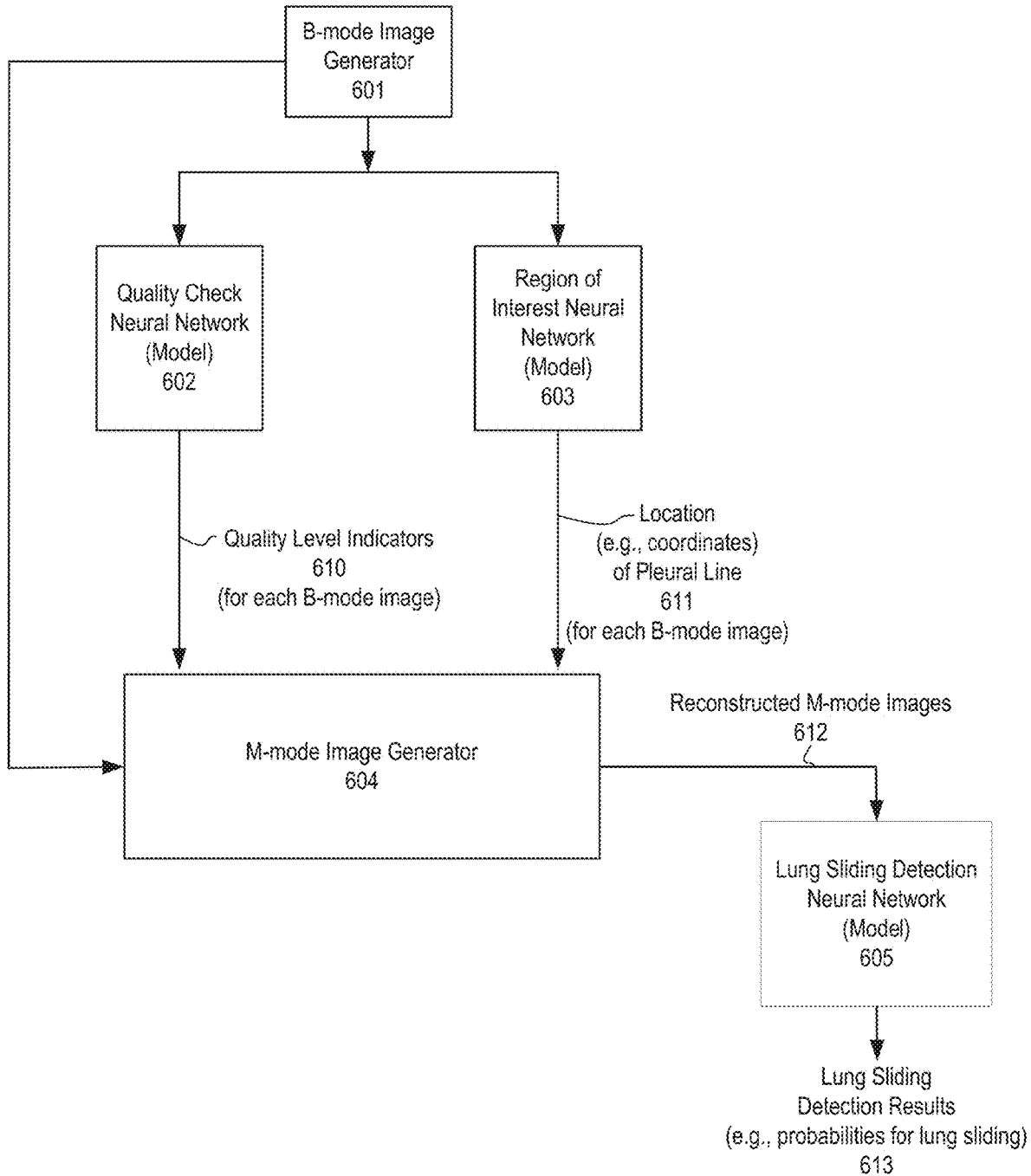
FIG. 6 illustrates some embodiments of a system for performing lung sliding detection processing.

FIG. 6 illustrates some embodiments of system for performing lung sliding detection processing. Referring to FIG. 6, B-mode images 601 are provided to quality check neural network (model) 602 and region of interest neural network (model) 603. In one embodiment, the quality check neural network (model) 602 and the region of interest neural network (model) 603 are separate neural networks. In some embodiments, these neural networks are combined into one neural network. In still other embodiments, these networks share at least one common part and include other parts that are not shared between these networks.

Quality check neural network 602 receives B-mode images 601 and determines whether each of B-mode images 601 is of sufficient quality to be used in the lung sliding detection process. Quality check neural network 602 determines the quality as described above and outputs quality level indications 610 for each of the B-mode images. In some embodiments, the quality is output for display on a display screen (e.g., the display screen of an ultrasound machine, etc.) for the user to guide and improve their image acquisition.

Region of interest neural network 603 receives B-mode images 601 and determines the location of the pleural line 611. ROI neural network 603 outputs location information 611 for each of the B-mode images. In some embodiments, the location information includes sets of coordinates of the end points of the pleural line. In some embodiments, the coordinates are x, y coordinates of the end points of the pleural line in each of the B-mode images.

Quality level indication information 610 and location information 611 are input to M-mode image generator 604 along with B-mode images 601. In response to these inputs, M-mode image generator 604 generates reconstructed M-mode images 612. In some embodiments, M-mode image generator 604 generates reconstructed M-mode images 612 from B-mode images as described above. Additionally or alternatively, the M-mode images can be obtained through a well-known M-mode image acquisition process.

Lung sliding detection neural network (model) 605 receives reconstructed M-mode images 612 and performs lung sliding detection on reconstructed M-mode images 612. In some embodiments, lung sliding detection is performed as described above. As an output, lung sliding detection neural network 605 generates lung sliding detection results 613. In some embodiments, the lung sliding detection results 613 include probabilities associated with each of the images for lung sliding. The lung sliding detection results may be displayed on an ultrasound image, such as, for example, a B-mode image as described above. For example, the ultrasound system can display the lung sliding detection results as part of a heat bar as previously described, and/or as part of a binary icon that distinguishes lung sliding from no lung sliding, such as a thumbs up/thumbs down indicator.

One or more of the neural networks of FIG. 6 can be implemented in a number of different ways. In one embodiment, the neural networks include models that use an EfficientNet architecture, a convolutional neural network (CNN), and/or sequence models including recurrent neural networks (RNN). Note that the detection techniques described herein can be implemented with artificial intelligence (AI) or machine-learning (e.g., adaptive boosting (adaboost), deep-learning, supervised learning models, support vector machine (SVM), Gated Recurrent Unit (GRU), convolutional GRU (ConvGRU), long short-term memory (LSTM), etc., to process frame information in sequence, and the line), and/or another suitable detection method.

Example Flow Diagram of Lung Detection Processes

Figure 7:
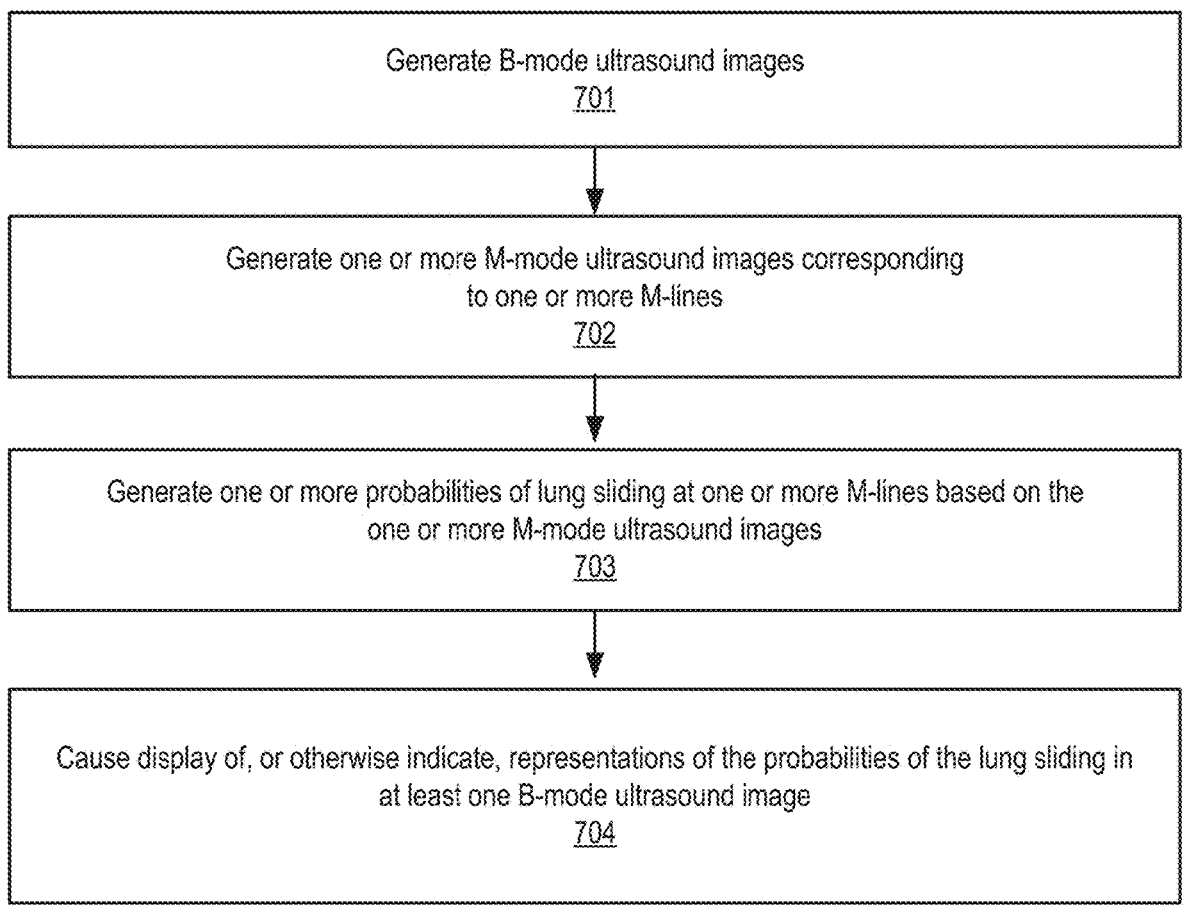
FIG. 7 is a data flow diagram of some embodiments of a lung sliding detection process.

FIG. 7 is a data flow diagram of some embodiments of a lung sliding detection process. The process can be performed by processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem.

Referring to FIG. 7, the process begins by processing logic (e.g., one or more memories) generates B-mode ultrasound images (processing block 701). Processing logic generates one or more M-mode ultrasound images corresponding to one or more M-lines (processing block 702). In some embodiments, the one or more M-mode images are generated based on the pixels of the B-mode images and the one or more M-lines.

Processing logic generates one or more probabilities of lung sliding at one or more M-lines based on the one or more M-mode ultrasound images (processing block 703). In one embodiment, processing logic generates the one or more probabilities of lung sliding at the one or more M-lines using a neural network. In some embodiments, the neural network is implemented at least partially in hardware of a computing device.

After generating the one or more probabilities of lung sliding at one or more M-lines, processing logic causes the display of representations of, or otherwise indicates, the probabilities of the lung sliding in at least one B-mode ultrasound image (processing block 704).

Figure 8:
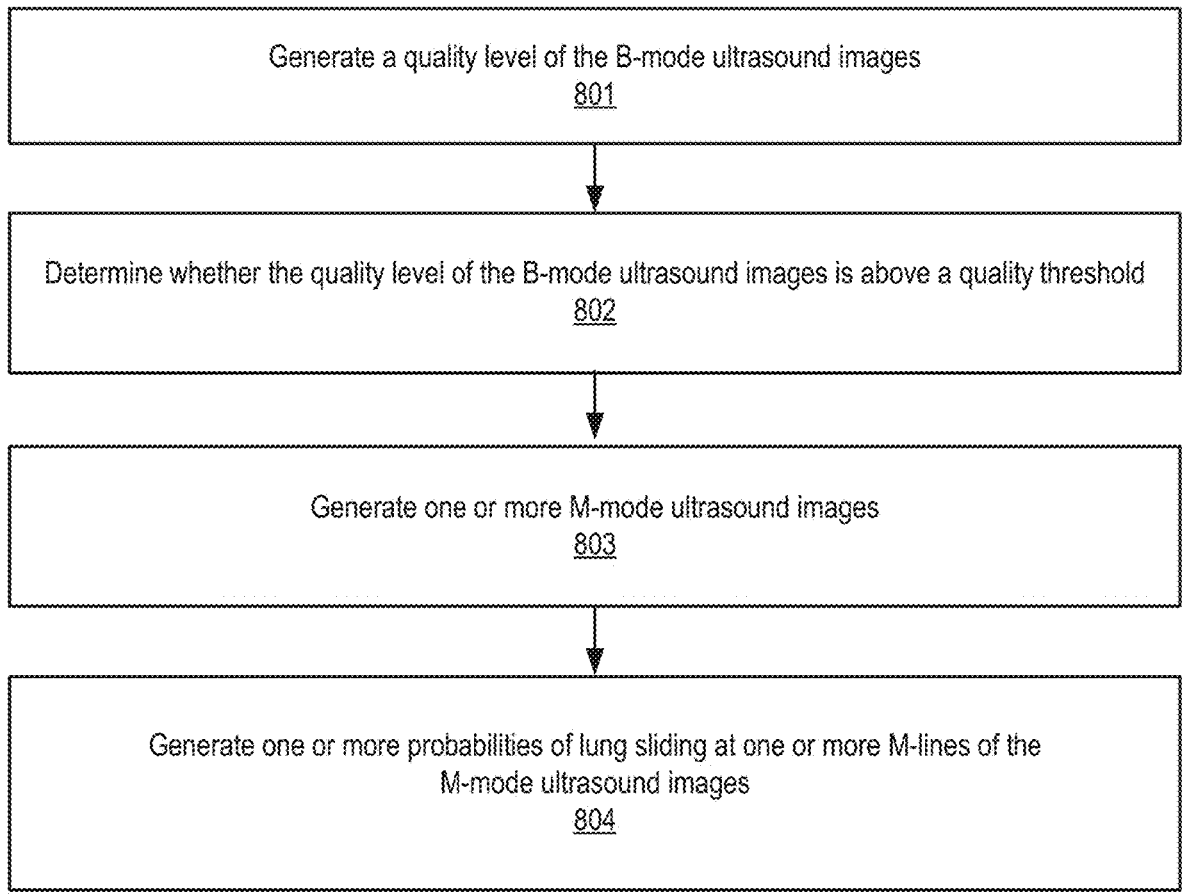
FIG. 8 is a flow diagram of some embodiments of a process for generating M-mode ultrasound images from B-mode ultrasound images.

FIG. 8 is a flow diagram of some embodiments of a process for generating M-mode ultrasound images from B-mode ultrasound images. The process can be performed by processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem.

Referring to FIG. 8, the process begins by processing logic generating a quality level of the B-mode ultrasound images (processing block 801) and determining whether the quality level of the B-mode ultrasound images is above a quality threshold (processing block 802). In one embodiment, processing logic generates the quality level of the B-mode ultrasound images based on attribute quality probabilities and pairs of coordinates. Examples of attribute quality probabilities include probabilities for attribute qualities including a resolution, a gain, a brightness, a clarity, a centeredness, a depth, a recognition of the pleural line, a recognition of a rib, and the like. In some embodiments, processing logic generates the attribute quality probabilities for the B-mode images and pairs of coordinates that indicate edges (e.g., end points) of a pleural line in the B-mode images. In some embodiments, processing logic generates the attribute quality probabilities using a neural network. In some embodiments, the neural network is implemented at least partially of hardware of a computing device.

After determining whether the quality level is above a quality threshold, processing logic generates one or more M-mode ultrasound images (processing block 803). In some embodiments, processing logic generates one or more M-mode ultrasound images in response to the quality level being above the quality threshold. In other words, the M-mode ultrasound images are only generated if the quality of the B-mode images is above the quality threshold Thereafter, processing logic then generates one or more probabilities of lung sliding at one or more M-lines of the M-mode ultrasound images (processing block 804). In some embodiments, the one or more probabilities are based on the M-mode ultrasound images generated from the B-mode ultrasound images.

Figure 9A:
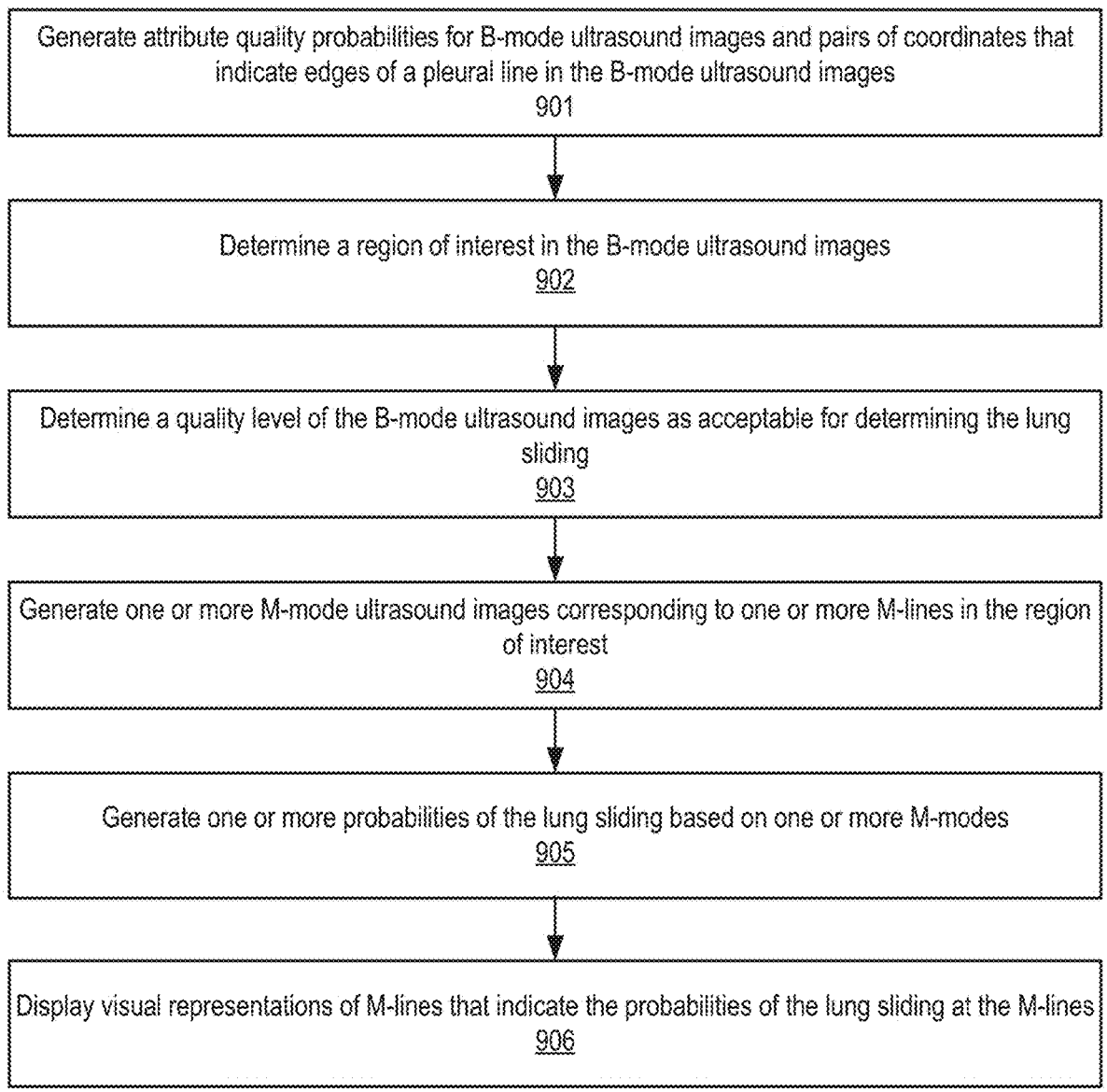
FIG. 9A is a flow diagram of some embodiments of a process for determining lung sliding.

FIG. 9A is a flow diagram of some embodiments of a process for determining lung sliding. The process can be performed by processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem.

Referring to FIG. 9A, the process begins by generating attribute quality probabilities for B-mode ultrasound images and pairs of coordinates that indicate edges of a pleural line in the B-mode ultrasound images (processing block 901). In some embodiments, these attribute quality probabilities for B-mode ultrasound images and pairs of coordinates are generated with a first neural network implemented at least partially in hardware of a computing device.

Next, processing logic determines a region of interest in the B-mode ultrasound images (processing block 902). In some embodiments, the region of interest in the B-mode ultrasound images is determined based on the previously-generated pairs of coordinates.

Processing logic also determines a quality level of the B-mode ultrasound images as acceptable for determining the lung sliding (processing block 903). In some embodiments, the determination that the B-mode ultrasound images have a quality level that is acceptable for determining the lung sliding is determined based on the previously-generated attribute quality probabilities and an amount of motion in the region of interest. In some embodiments, the attribute quality probabilities indicate a probability of at least one attribute quality taken from the group consisting of resolution, gain, brightness, clarity, centeredness, depth, recognition of the pleural line, and recognition of a rib.

In some embodiments, determining the quality level as acceptable includes, for each of the B-mode ultrasound images, determining a horizontal span of the pleural line and comparing the horizontal span to a threshold distance. In some embodiments, determining the horizontal span of the pleural line is performed based on horizontal components of the pairs of coordinates. In some embodiments, the process includes processing logic setting the threshold distance to be a percentage of a size of at least one of the B-mode ultrasound images. For example, in some embodiments, to be considered good quality, the pleural line must be located between 20% and 60% of the image vertically and the pleural line should cross the middle of the image. In some embodiments, determining the quality level as acceptable includes, for each of the B-mode ultrasound images, determining a depth of said each of the B-mode ultrasound images based on vertical components of the pairs of coordinates.

Using the B-mode ultrasound images, processing logic generates one or more M-mode ultrasound images corresponding to one or more M-lines in the region of interest (processing block 904). In some embodiments, the M-mode ultrasound images are from columns of pixels in each of the B-mode ultrasound images that correspond to the one or more M-lines.

Based on the one or more M-mode ultrasound images, processing logic generates probabilities of the lung sliding at the one or more M-lines (processing block 905). In some embodiments, processing logic generates probabilities of the lung sliding at the one or more M-lines with a neural network. The neural network may be implemented at least partially in the hardware of the computing device (e.g., an ultrasound machine, such as the ultrasound system 130 in FIG. 1).

Processing logic may also display visual representations of the one or more M-lines that indicate the probabilities of the lung sliding at the one or more M-lines (processing block 906). Color-coded versions of the M-lines 512 drawn in FIG. 5B are examples of the visual representations of the one or more M-lines that indicate the probabilities with colors. In some embodiments, processing logic displays the representations of these M-lines in a B-mode ultrasound image. In some embodiments, processing logic displays the visual representation horizontally across the region of interest, such as via a heat bar, as previously described. In some embodiments, the process of generating the visual representation includes processing logic filtering the probabilities. The probabilities may be filtered with a smoothing function in a horizontal direction.

In some embodiments, the one or more M-mode ultrasound images include multiple M-mode ultrasound images and the one or more M-lines include multiple M-lines across the region of interest. In some embodiments, in such a case, the process generates a visual representation of the probabilities of the lung sliding at the multiple M-lines and displays the visual representation horizontally across the region of interest.

In such a case, processing logic can generate the multiple M-mode ultrasound images based on a first start frame of the B-mode ultrasound images. In some embodiments, the process includes generating additional M-mode ultrasound images based on a second start frame of the B-mode ultrasound images and generating additional probabilities of the lung sliding at the multiple M-lines. The process also includes combining the probabilities and the additional probabilities to form combined probabilities of the lung sliding at the multiple M-lines. After forming the combined probabilities, the process generates and displays a visual representation of the combined probabilities. In some embodiments, processing logic generates the additional probabilities of the lung sliding at the multiple M-lines with a neural network and based on the additional M-mode ultrasound images.

Figure 9B:
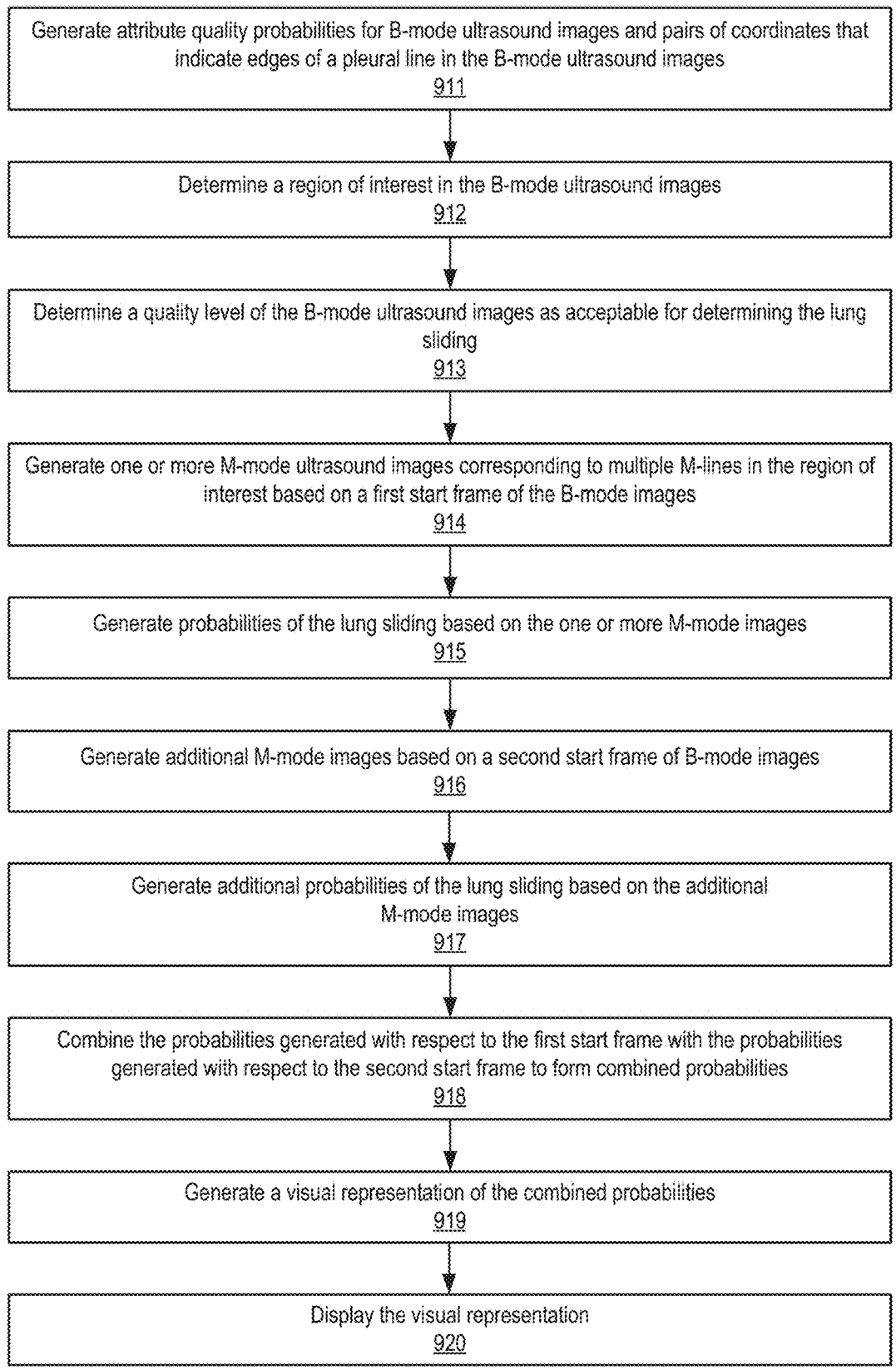
FIG. 9B illustrates some embodiments of a process for determining lung sliding in which additional probabilities of the lung sliding are generated and combined with other probabilities of lung sliding.

FIG. 9B illustrates some embodiments of a process for determining lung sliding in which the additional probabilities of the lung sliding are generated and combined with other probabilities of lung sliding. The process can be performed by processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging subsystem.

Referring to FIG. 9B, the process begins by generating attribute quality probabilities for B-mode ultrasound images and pairs of coordinates that indicate edges of a pleural line in the B-mode ultrasound images (processing block 911). In some embodiments, these attribute quality probabilities for B-mode ultrasound images and pairs of coordinates are generated with a first neural network implemented at least partially in hardware of a computing device.

Next, processing logic determines a region of interest in the B-mode ultrasound images (processing block 912). In some embodiments, the region of interest in the B-mode ultrasound images is determined based on the previously-generated pairs of coordinates.

Processing logic also determines a quality level of the B-mode ultrasound images as acceptable for determining the lung sliding (processing block 913). In some embodiments, the determination that the B-mode ultrasound images have a quality level that is acceptable for determining the lung sliding is determined based on the previously-generated attribute quality probabilities and an amount of motion in the region of interest. In some embodiments, the attribute quality probabilities indicate a probability of at least one attribute quality taken from the group consisting of resolution, gain, brightness, clarity, centeredness, depth, recognition of the pleural line, and recognition of a rib.

In some embodiments, determining the quality level as acceptable includes, for each of the B-mode ultrasound images, determining a horizontal span of the pleural line and comparing the horizontal span to a threshold distance. In some embodiments, determining the horizontal span of the pleural line is performed based on horizontal components of the pairs of coordinates. In some embodiments, the process includes processing logic setting the threshold distance to be a percentage of a size of at least one of the B-mode ultrasound images. For example, in some embodiments, to be considered good quality, the pleural line must be located between 20% and 60% of the image vertically and the pleural line should cross the middle of the image. In some embodiments, determining the quality level as acceptable includes, for each of the B-mode ultrasound images, and determining a depth of each of these B-mode ultrasound images based on vertical components of the pairs of coordinates.

Using the B-mode ultrasound images, processing logic generates one or more M-mode ultrasound images corresponding to one or more M-lines in the region of interest (processing block 914). In some embodiments, the M-mode ultrasound images are from columns of pixels in each of the B-mode ultrasound images that correspond to the one or more M-lines.

Based on the one or more M-mode ultrasound images, processing logic generates probabilities of the lung sliding based on one or more M-mode images (e.g., at the one or more M-lines) (processing block 915). In some embodiments, processing logic generates probabilities of the lung sliding at the one or more M-lines with a neural network. The neural network may be implemented at least partially in the hardware of the computing device (e.g., an ultrasound machine, such as the ultrasound system 130 in FIG. 1).

Processing logic then generates additional M-mode ultrasound images based on a second start frame of the B-mode ultrasound images (processing block 916) and additional probabilities of the lung sliding based on the additional M-mode ultrasound images (processing block 917). In some embodiments, these are generated in the same manner as described above in conjunction with processing blocks 914 and 915.

Processing logic combines the multiple probabilities generated from processing block 915 with the additional probabilities to form combined probabilities of the lung sliding (processing block 916).

Processing logic may also generate a visual representation of the combined probabilities (processing block 919) and display the visual representation (processing block 920). Color-coded versions of the M-lines 512 drawn in FIG. 5B are examples of the visual representations of the one or more M-lines that indicate the probabilities with colors. In some embodiments, processing logic displays the representations of these M-lines in a B-mode ultrasound image. In some embodiments, processing logic displays the visual representation horizontally across the region of interest, such as via a heat bar, as previously described. In some embodiments, the process of generating the visual representation includes processing logic filtering the probabilities. The probabilities may be filtered with a smoothing function in a horizontal direction.

Figure 10:
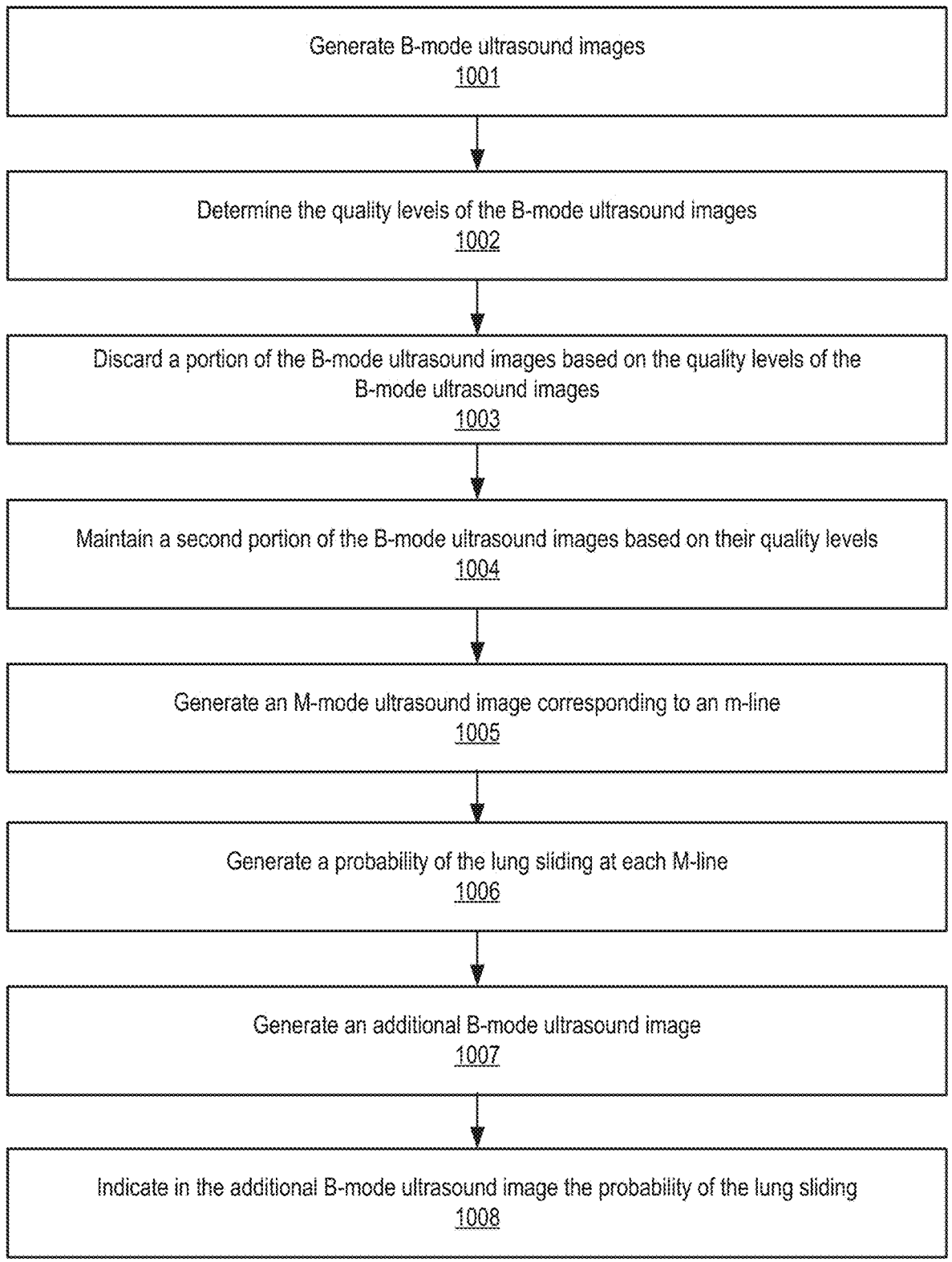
FIG. 10 is a flow diagram of some embodiments of another process for determining lung sliding.

FIG. 10 is a flow diagram of some embodiments of another process for determining lung sliding. The process can be performed by processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device such as, for example, but not limited to, an ultrasound machine with an ultrasound imaging system.

Referring to FIG. 10, the process begins by generating B-mode ultrasound images (processing block 1001). In some embodiments, the B-mode ultrasound images are generated in a manner well-known in the art.

In some embodiments, processing logic determines the quality levels of the B-mode ultrasound images (processing block 1002). In some embodiments, processing logic determines the quality levels using a process that includes generating pairs of coordinates that indicate edges of a pleural line in the B-mode ultrasound images, determining a region of interest in the B-mode ultrasound images based on the pairs of coordinates, and determining an amount of motion in the region of interest. In some embodiments, the pairs of coordinates that indicate edges of a pleural line in the B-mode ultrasound images are generated with a neural network. The neural network may be in addition to the neural network that generates probabilities of lung sliding at an M-line. In some embodiments, the neural network that generates the pairs of coordinates is implemented at least partially in the hardware of the ultrasound system.

In some embodiments, processing logic determines the quality levels using a process that includes generating, with an additional neural network implemented at least partially in the hardware of the ultrasound system, pairs of coordinates that indicate edges of a pleural line in the B-mode ultrasound images. The process for determining the quality levels can also include determining a horizontal span of the pleural line based on the pairs of coordinates, and comparing the horizontal span to a threshold distance. In some embodiments, the processing logic generates pairs of coordinates that indicate edges of a pleural line in the B-mode ultrasound images using a neural network. The neural network can be in addition to the neural network that generates probabilities of lung sliding at an M-line. In some embodiments, the neural network that generates the pairs of coordinates is implemented at least partially in the hardware of the ultrasound system.

In some embodiments, processing logic determines the quality levels using a process that includes generating attribute quality probabilities for the B-mode ultrasound images that indicate a probability of at least one attribute quality taken from the group consisting of a resolution, a gain, a brightness, a clarity, a centeredness, a depth, a recognition of a pleural line, and a recognition of a rib. In some embodiments, processing logic generates attribute quality probabilities for the B-mode ultrasound images using a neural network. The neural network may be in addition to the neural network that generates probabilities of lung sliding at an M-line. In some embodiments, the neural network that generates the attribute quality probabilities is implemented at least partially in the hardware of the ultrasound system.

Then processing logic discards a first portion of the B-mode ultrasound images based on the quality levels of the B-mode ultrasound images (processing block 1003) while maintaining a second portion of the B-mode ultrasound images based on their quality levels (processing block 1004). In some embodiments, the probability of the lung sliding is based on the retained portion of the B-mode ultrasound images. Note also that in some embodiments, the quality may also be displayed to the user.

Using the retained B-mode ultrasound images, processing logic generates an M-mode ultrasound image corresponding to an M-line (processing block 1005). Note that this process may be repeated such that multiple M-mode ultrasound images are generated. In some embodiments, processing logic generates the M-mode images based on pixels in the B-mode ultrasound images that correspond to the M-line.

Based on the M-mode ultrasound image, processing logic generates a probability of the lung sliding at each M-line (processing block 1006). In some embodiments, processing logic generates a probability of the lung sliding at the M-line using a neural network. In some embodiments, the neural network is implemented at least partially in the hardware of the ultrasound system.

After generating a probability of the lung sliding at the M-line, processing logic generates an additional B-mode ultrasound image (processing block 1007) and indicates in the additional B-mode ultrasound image the probability of the lung sliding (processing block 1008).

The systems, devices, and methods disclosed herein constitute numerous advantages over conventional ultrasound systems, devices and methods that do not implement automated detection of lung slide to aid in the diagnosis of PTX. For instance, the ultrasound systems disclosed herein can reliably diagnose PTX in real-time with portable ultrasound equipment, which simply cannot be done with conventional ultrasound systems due to the time required to operate the conventional ultrasound systems and the errors introduced by the operator. Consequently, the ultrasound systems can more accurately and more quickly diagnose PTX than conventional ultrasound systems and have lifesaving impacts at the point of care.

Moreover, by using the ultrasound systems disclosed herein, the burden of resources of a care facility is reduced compared to the use of conventional ultrasound systems. This advantage is because the use of the ultrasound systems disclosed herein can result in successful diagnosis of PTX with the ultrasound system alone, without the need to send patients to another imaging department, such as a radiology department. In contrast, because conventional ultrasound systems may not suitably diagnosis PTX, as described above, they may require the use of additional imaging, and therefore place higher burdens on the resources of the care facility than the ultrasound systems disclosed herein. Hence, the ultrasound systems disclosed herein can make the care facility operate more efficiently and thus provide better patient care, compared to conventional ultrasound systems.

Further, because the ultrasound systems disclosed herein operate more quickly than conventional ultrasound systems that do not implement automated detection of lung slide to aid in the diagnosis of PTX, the operator can perform a more comprehensive ultrasound examination in a given amount of time using the ultrasound systems disclosed herein compared to conventional ultrasound systems. Accordingly, the patient may receive better care with the ultrasound systems disclosed herein compared to conventional ultrasound systems. Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

We claim:

1. A method implemented by a computing device for determining lung sliding, the method comprising:
   generating attribute quality probabilities for B-mode ultrasound images that include a pleural line;
   determining, based on the attribute quality probabilities, a quality level of the B-mode ultrasound images as acceptable for said determining the lung sliding;
   generating one or more M-mode ultrasound images based on the B-mode ultrasound images; and
   generating, based on the one or more M-mode ultrasound images, one or more probabilities of the lung sliding.

2. The method as described in claim 1, wherein the attribute quality probabilities indicate a probability of at least one attribute quality taken from the group consisting of a resolution, a gain, a brightness, a clarity, a centeredness, a depth, a recognition of the pleural line, and a recognition of a rib.

3. The method as described in claim 1, wherein the generating the attribute quality probabilities includes generating, with a first neural network implemented at least partially in hardware of the computing device, the attribute quality probabilities, and the generating the one or more probabilities of the lung sliding includes generating, with a second neural network implemented at least partially in the hardware of the computing device, the one or more probabilities of the lung sliding.

4. The method as described in claim 1, further comprising:
   generating coordinates that indicate end points of the pleural line;
   determining, based on the coordinates, a region of interest in the B-mode ultrasound images; and
   determining an amount of motion in the region of interest;
   wherein the determining the quality level as acceptable is based on the amount of motion.

5. The method as described in claim 1, further comprising:
   generating coordinates that indicate end points of the pleural line;
   determining, based on the coordinates, a horizontal span of the pleural line; and comparing the horizontal span to a threshold distance;
   wherein the determining the quality level as acceptable is based on the comparing.

6. The method as described in claim 5, further comprising setting the threshold distance as a percentage of a size of at least one of the B-mode ultrasound images.

7. The method as described in claim 1, further comprising generating coordinates that indicate end points of the pleural line;
   wherein the determining the quality level as acceptable includes, for each of the B-mode ultrasound images, determining a depth of said each of the B-mode ultrasound images based on the coordinates.

8. The method as described in claim 1, further comprising extracting one or more columns of pixels in each of the B-mode ultrasound images, the one or more columns of pixels corresponding to one or more M-lines;
  wherein the generating the one or more M-mode ultrasound images is based on the one or more columns of pixels, and the one or more probabilities of the lung sliding correspond to the one or more M-lines.

9. The method as described in claim 8, further comprising:
  generating one or more visual representations of the one or more M-lines, respectively, the one or more visual representations indicating the one or more probabilities of the lung sliding at the one or more M-lines; and
  displaying, in at least one B-mode ultrasound image of the B-mode ultrasound images, the one or more visual representations.

10. The method as described in claim 1, wherein the one or more M-mode ultrasound images include multiple M-mode ultrasound images, the one or more probabilities include multiple probabilities, and the generating the multiple M-mode ultrasound images is based on a first start frame of the B-mode ultrasound images, further comprising:
  generating additional M-mode ultrasound images based on a second start frame of the B-mode ultrasound images;
  generating additional probabilities of the lung sliding based on the additional M-mode ultrasound images;
  combining the multiple probabilities and the additional probabilities to form combined probabilities of the lung sliding;
  generating a visual representation of the combined probabilities; and
  displaying the visual representation.

11. The method as described in claim 1, wherein the one or more M-mode ultrasound images include multiple M-mode ultrasound images corresponding to multiple M-lines across a region of interest in the B-mode ultrasound images, and the one or more probabilities include multiple probabilities of the lung sliding at the multiple M-lines, further comprising:
  generating a visual representation of the multiple probabilities of the lung sliding at the multiple M-lines; and
  displaying the visual representation horizontally across the region of interest.

12. The method as described in claim 11, wherein the generating the visual representation includes filtering the multiple probabilities with a smoothing function in a horizontal direction.

13. A method implemented by a computing device for determining lung sliding, the method comprising:
  generating B-mode ultrasound images;
  generating an M-mode ultrasound image corresponding to an M-line;
  generating, based on the M-mode ultrasound image, a probability of the lung sliding at the M-line;
  indicating in at least one B-mode ultrasound image of the B-mode ultrasound images the probability of the lung sliding;
  determining quality levels of the B-mode ultrasound images;
  discarding a first portion of the B-mode ultrasound images based on the quality levels of the B-mode ultrasound images in the first portion;
  maintaining a second portion of the B-mode ultrasound images based on the quality levels of the B-mode ultrasound images in the second portion, wherein the generating the probability of the lung sliding is based on the second portion of the B-mode ultrasound images;
  generating a visual representation of the quality levels of the B-mode ultrasound images; and
  displaying the visual representation in at least one of the B-mode ultrasound images for guiding ultrasound probe placement.

14. The method as described in claim 13, wherein the generating the M-mode ultrasound image is based on pixels in the B-mode ultrasound images that correspond to the M-line.

15. A method implemented by a computing device for determining lung sliding, the method comprising:
  generating B-mode ultrasound images;
  generating an M-mode ultrasound image corresponding to an M-line;
  generating, based on the M-mode ultrasound image, a probability of the lung sliding at the M-line;
  indicating in at least one B-mode ultrasound image of the B-mode ultrasound images the probability of the lung sliding;
  determining quality levels of the B-mode ultrasound images;
  discarding a first portion of the B-mode ultrasound images based on the quality levels of the B-mode ultrasound images in the first portion;
  maintaining a second portion of the B-mode ultrasound images based on the quality levels of the B-mode ultrasound images in the second portion, wherein the generating the probability of the lung sliding is based on the second portion of the B-mode ultrasound images,
  wherein the determining the quality levels includes:
  generating coordinates that indicate end points of a pleural line in the B-mode ultrasound images;
  determining, based on the coordinates, a region of interest in the B-mode ultrasound images; and
  determining an amount of motion in the region of interest.

16. A method implemented by a computing device for determining lung sliding, the method comprising:
  generating B-mode ultrasound images;
  generating an M-mode ultrasound image corresponding to an M-line;
  generating, based on the M-mode ultrasound image, a probability of the lung sliding at the M-line;
  indicating in at least one B-mode ultrasound image of the B-mode ultrasound images the probability of the lung sliding;
  determining quality levels of the B-mode ultrasound images;
  discarding a first portion of the B-mode ultrasound images based on the quality levels of the B-mode ultrasound images in the first portion;
  maintaining a second portion of the B-mode ultrasound images based on the quality levels of the B-mode ultrasound images in the second portion, wherein the generating the probability of the lung sliding is based on the second portion of the B-mode ultrasound images, wherein the determining the quality levels includes:
  generating coordinates that indicate end points of a pleural line in the B-mode ultrasound images;
  determining, based on the coordinates, a horizontal span of the pleural line; and
  comparing the horizontal span to a threshold distance.

17. A computing device to implement an ultrasound system for determining lung sliding, the computing device comprising:

a memory to maintain B-mode ultrasound images and one or more M-mode ultrasound images;

a neural network implemented at least partially in hardware of the computing device to generate, based on the one or more M-mode ultrasound images, one or more probabilities of the lung sliding at one or more M-lines; and a processor system to:

generate, based on pixels in the B-mode ultrasound images that correspond to the one or more M-lines, the one or more M-mode ultrasound images corresponding to the one or more M-lines;

cause display in at least one of the B-mode ultrasound images of one or more representations of the one or more probabilities of the lung sliding;

generate a quality level of the B-mode ultrasound images;

determine whether the quality level is above a quality threshold; and generate the one or more M-mode ultrasound images responsive to the quality level being above the quality threshold.

* * * * *